(12) United States Patent
Hequet et al.

(10) Patent No.: US 6,520,007 B2
(45) Date of Patent: Feb. 18, 2003

(54) COTTON STICKINESS EVALUATION BY MEANS OF MULTI-TEMPERATURE TESTING

(75) Inventors: Eric Francois Hequet, Lubbock, TX (US); Noureddine Abidi, Lubbock, TX (US)

(73) Assignee: Texas Tech University, Lubbock, TX (US)

( * ) Notice: Subject to any disclaimer, the term of this patent is extended or adjusted under 35 U.S.C. 154(b) by 0 days.

(21) Appl. No.: 09/753,716

(22) Filed: Jan. 4, 2001

(65) Prior Publication Data

US 2002/0083764 A1 Jul. 4, 2002

(51) Int. Cl.$^7$ ................................................. G01L 5/04
(52) U.S. Cl. ....................................................... 73/159
(58) Field of Search .................. 73/866, 159; 19/66 CC

(56) References Cited

U.S. PATENT DOCUMENTS

| | | | |
|---|---|---|---|
| 5,153,968 A | * 10/1992 | Sterin et al. ................ | 19/66 |
| 5,636,546 A | 6/1997 | Frydrych | |
| 5,700,961 A | 12/1997 | Anthony | |
| 5,752,294 A | 5/1998 | Mor | |
| 5,942,689 A | 8/1999 | Bonissone | |
| 6,158,277 A | * 12/2000 | Artzt et al. ................ | 73/159 |

OTHER PUBLICATIONS

Ellsworth et al., Sticky Cotton Sources and Solutions, The University of Arizona Cooperative Extension, IPM Series No. 13 AZ1156, Dec. 1999.*

M. Dean Ethridge, Status of Research on the Meaning and Measurements of Cotton Stickiness, International Textile Center, Texas Tech University, The Cotton Gin and Oil Mill Press, Jun. 20, 1998.*

Hequet et al., How Cotton Stickiness Measurements Related to Spinning Efficiency, Texas Tech University, International Textile Center, Lubbock Texas.*

* cited by examiner

Primary Examiner—Hezron Williams
Assistant Examiner—C D Garber
(74) Attorney, Agent, or Firm—Jones, Tullar & Cooper, P.C.

(57) ABSTRACT

The stickiness of cotton is determined by testing a cotton sample at two or more temperatures. Sticky deposits are recorded at a lower temperature, preferably 27° C. or 34° C., to detect the trehalulose-rich honeydews droplets. Then, the sample is subjected to a higher temperature, preferably 54° C., to detect the non trehalulose-rich honeydew droplets and physiological sugars. By comparing the results at these two temperatures, an accurate grading system for cotton may be produced which can help growers and spinners accurately identify different types of cotton and determine processing problems.

20 Claims, 24 Drawing Sheets 20X    20X

FIG. 9b

| | Temperature reading in °C | | | | | | | | |
|---|---|---|---|---|---|---|---|---|---|
| | 1 | 2 | 3 | 4 | 5 | 6 | 7 | 8 | Av. |
| Card, 23°C/60%RH | | | | | | | | | |
| Licker-in | | | | | | | | | 29 |
| Main Cylinder | | | | | | | | | 34 |
| Flats | | | | | | | | | 30 |
| Doffer | | | | | | | | | 27 |
| Drawing, 23°C/55%RH | | | | | | | | | |
| Back roll | 37 | 38 | 38 | 38 | 38 | 38 | 38 | 38 | 38 |
| Middle roll | 42 | 42 | 42 | 42 | 42 | 42 | 42 | 42 | 42 |
| Front roll | 53 | 54 | 53 | 53 | 53 | 53 | 53 | 53 | 53 |
| Calendar roll | 40 | 40 | 41 | 41 | 40 | 40 | 41 | 41 | 41 |
| Roving, 23°C/55%RH | | | | | | | | | |
| Back roll | 26 | 26 | 26 | 26 | 26 | 26 | 26 | 26 | 26 |
| Middle roll | 28 | 28 | 28 | 28 | 28 | 28 | 28 | 28 | 28 |
| Front roll | 31 | 31 | 31 | 31 | 31 | 31 | 31 | 31 | 31 |
| Trumpet | 28 | 28 | 28 | 28 | 28 | 28 | 28 | 28 | 28 |
| Ring spinning, 23°C/62%RH | | | | | | | | | |
| Back roll | 25 | 25 | 24 | 24 | 24 | 25 | 25 | 24 | 25 |
| Middle apron | 26 | 26 | 26 | 26 | 26 | 26 | 26 | 26 | 26 |
| Front roll | 28 | 28 | 28 | 27 | 28 | 28 | 28 | 27 | 28 |
| Ring | 27 | 27 | 27 | 27 | 27 | 27 | 27 | 27 | 27 |
| Rotor spinning, 23°C/55%RH | | | | | | | | | |
| Feed plate | Not able to measure | | | | | | | | |
| Combing roll | 31 | 31 | 31 | 31 | 31 | 31 | 31 | 31 | 31 |
| Rotor | 36 | 37 | 37 | 36 | 37 | 37 | 37 | 37 | 37 |
| Navel | 38 | 37 | 38 | 39 | 37 | 36 | 37 | 38 | 38 |

COTTON STICKINESS EVALUATION BY MEANS OF MULTI-TEMPERATURE TESTING

BACKGROUND OF THE INVENTION

The present invention relates generally to a method for testing the stickiness of cotton using multiple temperatures.

In a spinning mill, cotton contaminated with excessive amounts of sugars causes serious problems, for it contaminates all the mechanical instruments used in the transformation process from fiber to yarn; i.e., opening, carding, drawing, roving and spinning operations. These contaminants are due mainly to sugar deposits produced either by the cotton plant itself (physiological sugars) or by feeding insects (entomological sugars).

The physiological sugars that are deposited on cotton have been analyzed using the aphis-stylet technique to obtain pure phloem sap from cotton plants to show that the major sugar translocated is sucrose (>90%). The presence of sucrose in the cotton lint reveals that the plant was still growing when the harvest occurred. Some sucrose was still translocated to the bolls in order to continue the growth process and to accumulate cellulose within the underdeveloped fibers. Mature bolls have low physiological sugar content, while immature bolls, still in the development phase, have high physiological sugar content. Also, harvest-aid chemicals cause some of these bolls to open. For this type of cotton plant the distribution of the sugars will not be even. The least developed fibers coming from such immature bolls tend to remain together in the form of entangled fibers and when ginned, the water content of this specific type of fibers at the breaking point is such that the physiological sugars are able to migrate from the inside of the fibers to the outside through the open lumen. This succession of events leads to a localized concentration of sugars similar to the one observed with honeydew.

Although the presence of physiological sugars is a problem when processing cotton, cotton stickiness is more often attributed to entomological sugars from insect honeydew than physiological sugars. The main honeydew-producing insects that infest cotton plants are the cotton white fly *Bemisia tabaci* (Gennadius) and the cotton aphid *Aphis gossypii* (Glover). White flies and aphids are both plant sap-sucking insects that feed by inserting their slender mouth-parts and the stylets into the leaf tissues. The sap is digested and ejected as a droplet of honeydew. The honeydew attaches itself to the leaves and the fibers of opened bolls. The ginning process scatters the honeydew, making it more difficult to detect with the naked eyes. Tests relating to these entomological sugars have been performed analyzing honeydew from *Aphis gossypii* and *Bemisia tabaci*. The testing found around 40% of melezitose in the aphid honeydew and 40% of trehalulose plus 17% of melezitose in the white fly honeydew. These percentages are different on contaminated lint water extract because of the physiological sugars.

Stickiness is a worldwide contamination problem as shown by the International Textile Manufacturers Federation (ITMF) Cotton Contamination Survey (Strolz, 2000). Every other year the ITMF organizes a survey by sending to spinners worldwide a questionnaire about the perception they have on the different cotton contaminations for the main origins of cotton. "In 1999, of the most important growths, Sudanese cottons remains the most affected with nearly 75% of all those having used these origins experiencing stickiness, followed by the average of all growths of West Africa (33.5%), Central Asia (25.3%), India (21.9%), and the US (18.6%). At the lower end of the scale follow Turkey (9%), Australia (9%) and Argentina (5%)." Because of this worldwide contamination problem a variety of testing procedures to determine the stickiness of cotton have been developed.

One of the testing procedures is the Potassium Ferricyanide Reducing Sugars Test (Perkins test), which is based on the hypothesis that stickiness is caused by reducing sugars, mainly glucose, fructose and oxidized trehalulose and sucrose. The test consists of oxidizing sugars by potassium ferricyanide ion in alkaline solution. Sugar solutions are reacted with standardized ferricyanide solution and titrated with ceric sulphate with ferrion as an indicator. The tests of total reducing sugars or total sugar content give no indication of the type of sugars involved in the stickiness phenomenon. In addition, melezitose being a non-reducing sugar is not detected by this method which leads to false positive results. Furthermore, this test gives no indication of the distribution of the sugars on the fiber. Since stickiness is mainly due to localized high sugar concentration (insect excrement) it is extremely important to get distribution information.

Another testing procedure is the High Performance Liquid Chromatography (HPLC), which is performed by first extracting sugars with water. By using an appropriate eluant, the sugar solution goes through a column where a separation takes place on the basis of molecular weight and steric arrangement. HPLC profiles indicate the amounts of individual sugars on the lint. Having a similar disadvantage as the Perkins test, this test cannot give information about sticky deposit distribution and therefore is not a good predictor of stickiness in the mill. In addition, this time consuming test is costly, which limits its utilization to research laboratories.

The Minicard test (Perkins, 1990) was approved by The International Textile Manufacturers as a reference test in 1990. A sample of 10 grams is processed through the minicard at 55% relative humidity. The sample is rated for stickiness depending upon its behavior as the card web passes between the stainless steel delivery rolls. For accurate evaluation, the instrument should be subjected to frequent cleaning. Consequently, this highly operator sensitive technique is not adequate for large scale testing.

The Fiber Contamination Tester (FCT) is derived from the minicard principle. A 3 grams sample (hand-sliver shaped) is processed through a micro-card at 65% relative humidity. Then the cotton web passes between 2 crush-rolls. The friction of the brushes (cleaning device) increases the temperature of the crush rolls and allows the honeydew to stick to the crush rolls. This unintentional temperature change makes the instrument a kind of "Thermodetector". The sticky deposits on the rolls are detected using laser beams. A cleaning device of brushes and knives removes the sticky deposits. Software analyses the electronic signal, providing the user with the number of deposits along with their size. The FCT is designed such that the instrument is very quickly contaminated with honeydew rendering the results questionable.

The Sticky Cotton Thermodetector (SCT) was approved as a reference test by the International Textile Manufacturers Federation in 1994. This thermo-mechanical method combines the effect of heat and pressure applied to a sample of cotton placed between two aluminum foils. When the temperature increases, the cotton releases its water, which is absorbed by the sticky spots making them stick to the foils. However, this instrument is operator sensitive and slow.

The High Speed Stickiness Detector (H2SD) is based on the SCT principle. First, a sample of cotton weighing between 3.0 and 3.5 g is opened using a rotor type opener. The mass of opened fiber is then shaped into a rectangular, even pad of fibers. This pad is deposited by the system on aluminum foil. Then, the sample passes successively in front of 4 stations. A hot pressure is applied to the sample (54 degrees C, 30 seconds). The combination of the free water molecules in the cotton lint and the temperature differential between the heat applied and the aluminun foil produces a thin layer of humidity on the sheet of aluminum. The sticky points in contact with the aluminum are fixed in place by pressure exerted at ambient temperature. The cotton is then removed and the sticky spots are counted and sized by an image analyzer. This testing procedure is undesirable because it may give false positive test results. This process does not give a realistic interpretation of the stickiness of the cotton at machine operating temperatures. Certain cottons contain sugar deposits that cause sticky spots at elevated temperatures, such as 54° C., but do not have sticky deposits at lower, operating temperatures, such as 27 ° C. This false result forces cotton growers to sell their crop to spinners at a discount.

BRIEF SUMMARY OF THE INVENTION

The present invention overcomes the above-mentioned problems by developing a method that is based on the detection of cotton stickiness at multiple temperatures. By testing the cotton stickiness at two or more temperatures, different grades of cotton can accurately be distinguished to allow growers and spinners to manage their crops.

Cotton may be tested for sticky deposits of sugars using at least two different temperatures. The cotton is tested at a lower temperature, preferably 27 ° C. or 34 ° C., to determine the amount of trehalulose-rich honeydew droplets. The cotton is then tested at a second temperature, preferably 54 ° C., to determine the amount of non trehalulose-rich honeydew droplets and physiological sugar. The amount of sticky spots at the two temperatures are compared to yield an accurate grading of cotton.

Due to the different thermal properties of sugars, the lowest temperature will render trehalulose (mainly present in white flies honeydew) stickier than the other types of sugars. Alternately, the higher temperatures will render the other sugars, present on the contaminated lint, stickier. The honeydew droplets having a high percentage of trehalulose will stick at any temperature. The lower the trehalulose percentage is in those droplets, the lower is the "sticky potential" at low temperature. The differential between two or more readings at different temperatures will show the type of contamination and will allow the spinners to better predict the processing troubles to be expected in the mill and to use this information for bale management.

BRIEF DESCRIPTION OF THE DRAWINGS

The features and advantages of the present invention will become apparent from the following detailed description of a preferred embodiment thereof, taken in conjunction with the accompanying drawings, in which:

FIG. 9b is a table of temperature measurements on processing equipment after temperature stabilization.

DESCRIPTION OF THE PREFERRED EMBODIMENT

Figure 1:
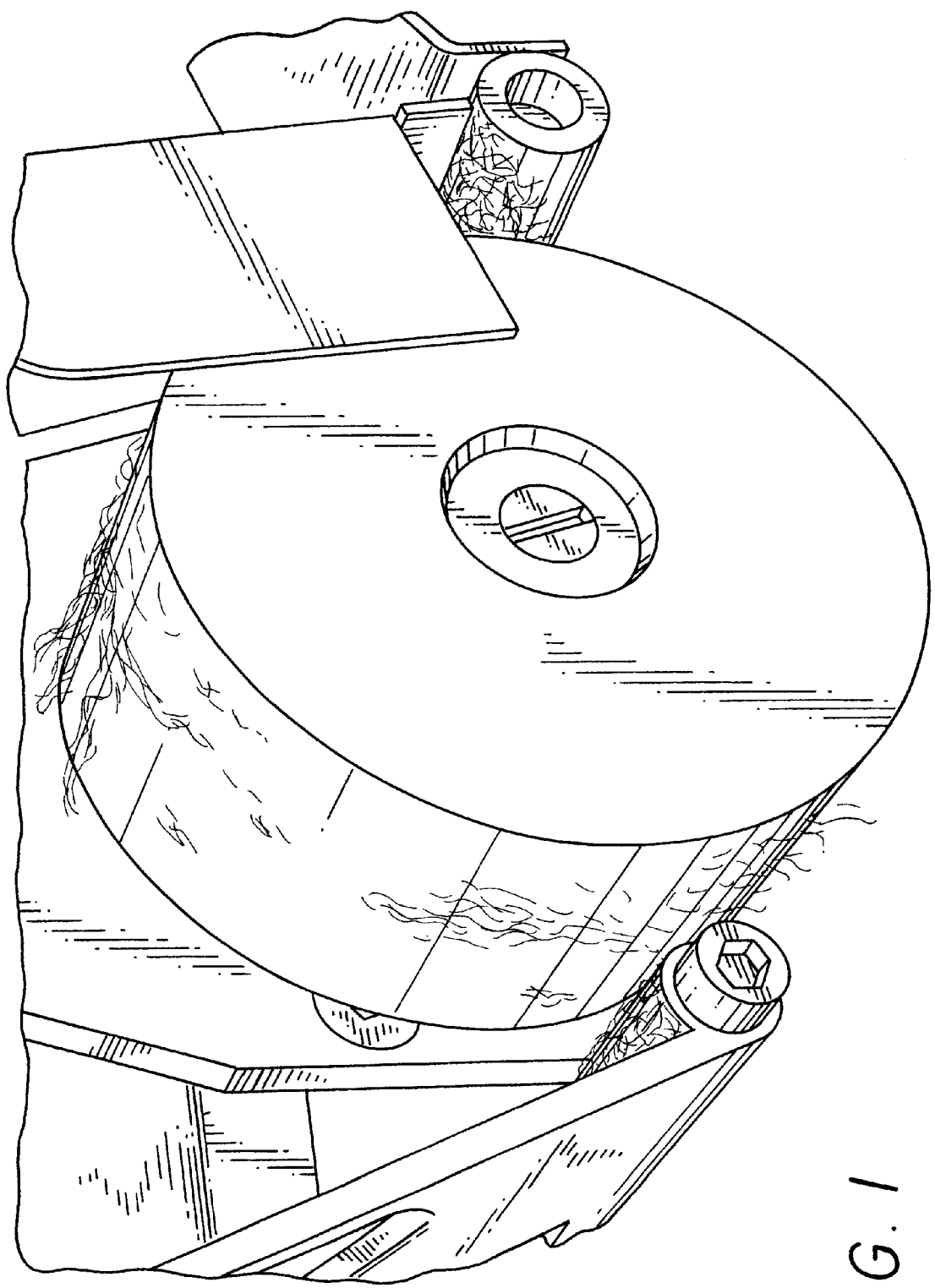
FIG. 1 shows the sticky deposits that appear on draw frame creels due to the sugars that contaminate cotton.
Figure 2:
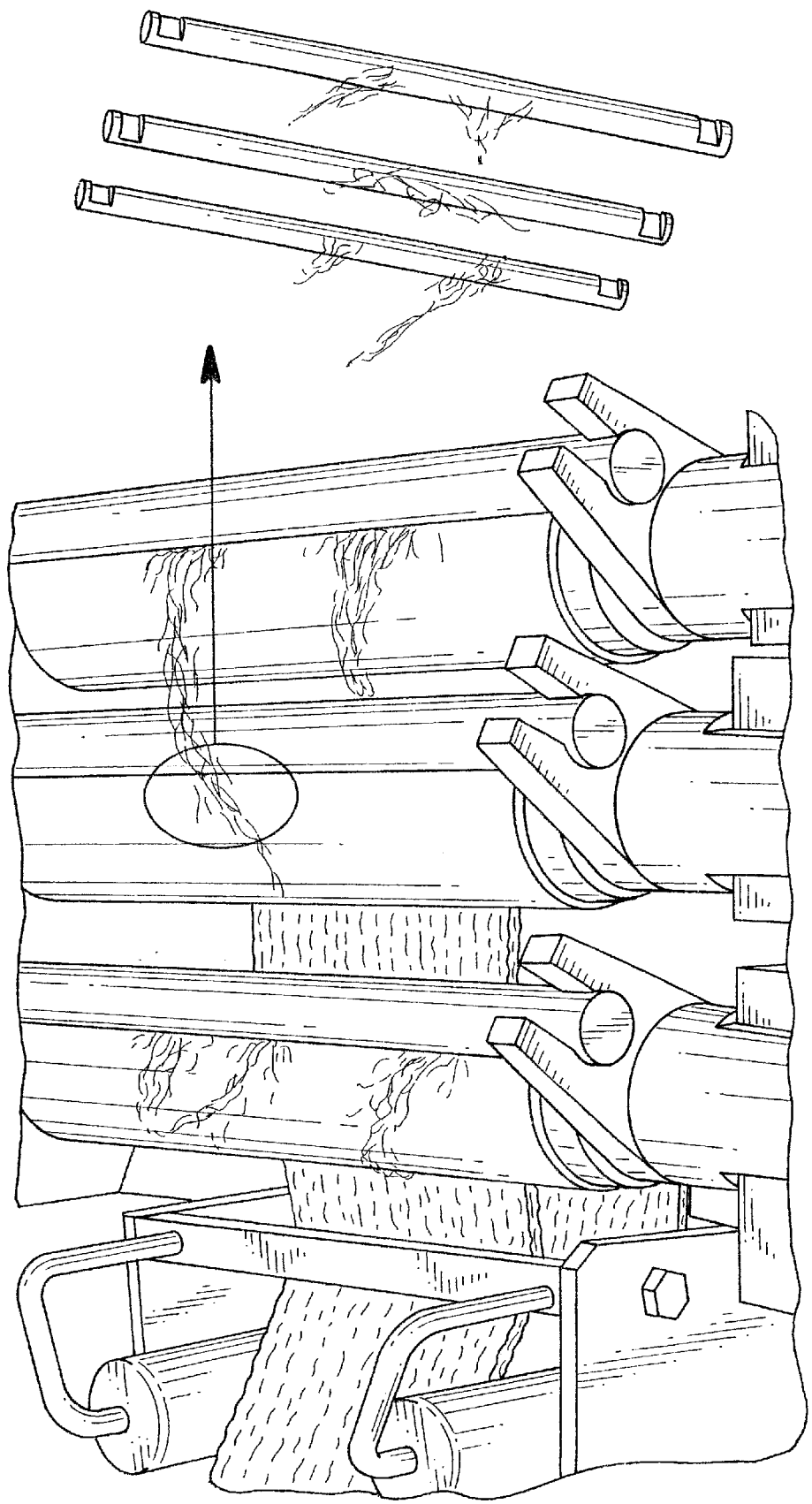
FIG. 2 shows the sticky deposits that appear on draw frames due to the sugars that contaminate cotton.
Figure 3:
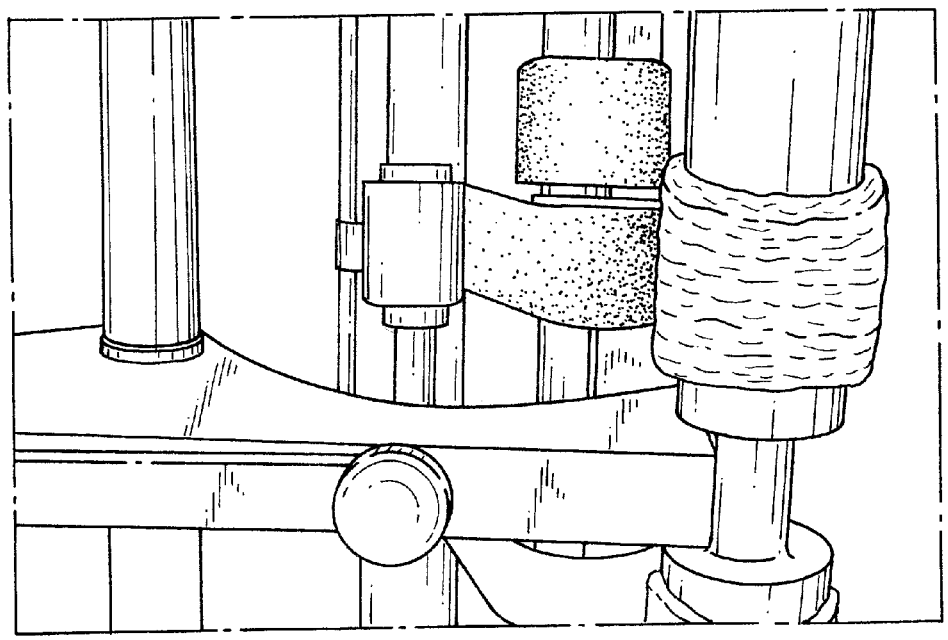
FIG. 3 shows the sticky deposits that appear on ring spinning frames due to the sugars that contaminate cotton.
Figure 3:
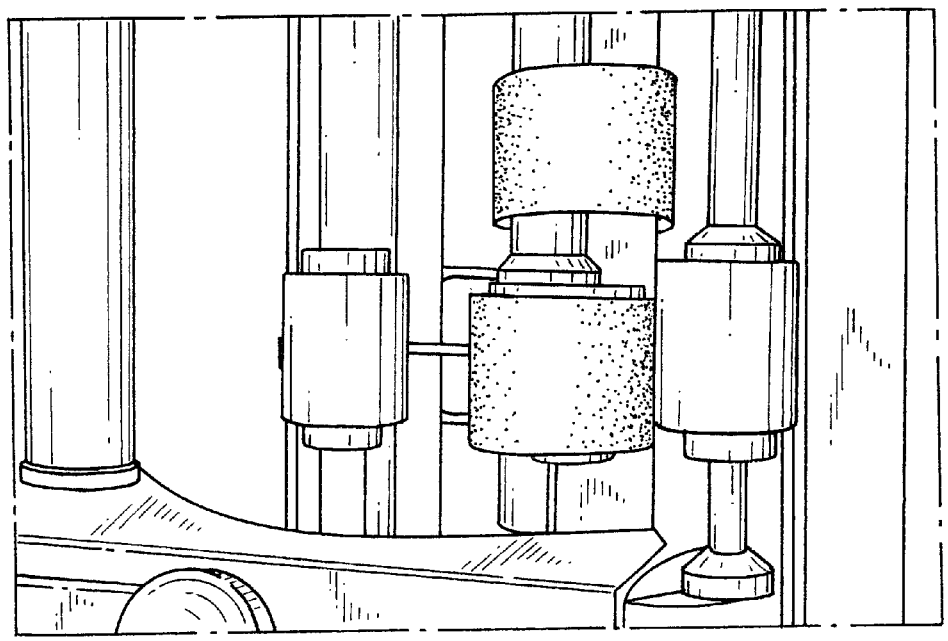

FIGS. 1–3 show typical problems that occur while processing contaminated cotton fibers. FIG. 1 shows the problems that occur on draw frame creels due to the stickiness problems related to cotton contaminates. FIG. 2 shows the problems that can occur on dram frames due to the sticky deposits left by cotton. FIG. 3 shows the problems that occur on ring spinning frames because of the sticky deposits left from cotton processing.

Figure 4:
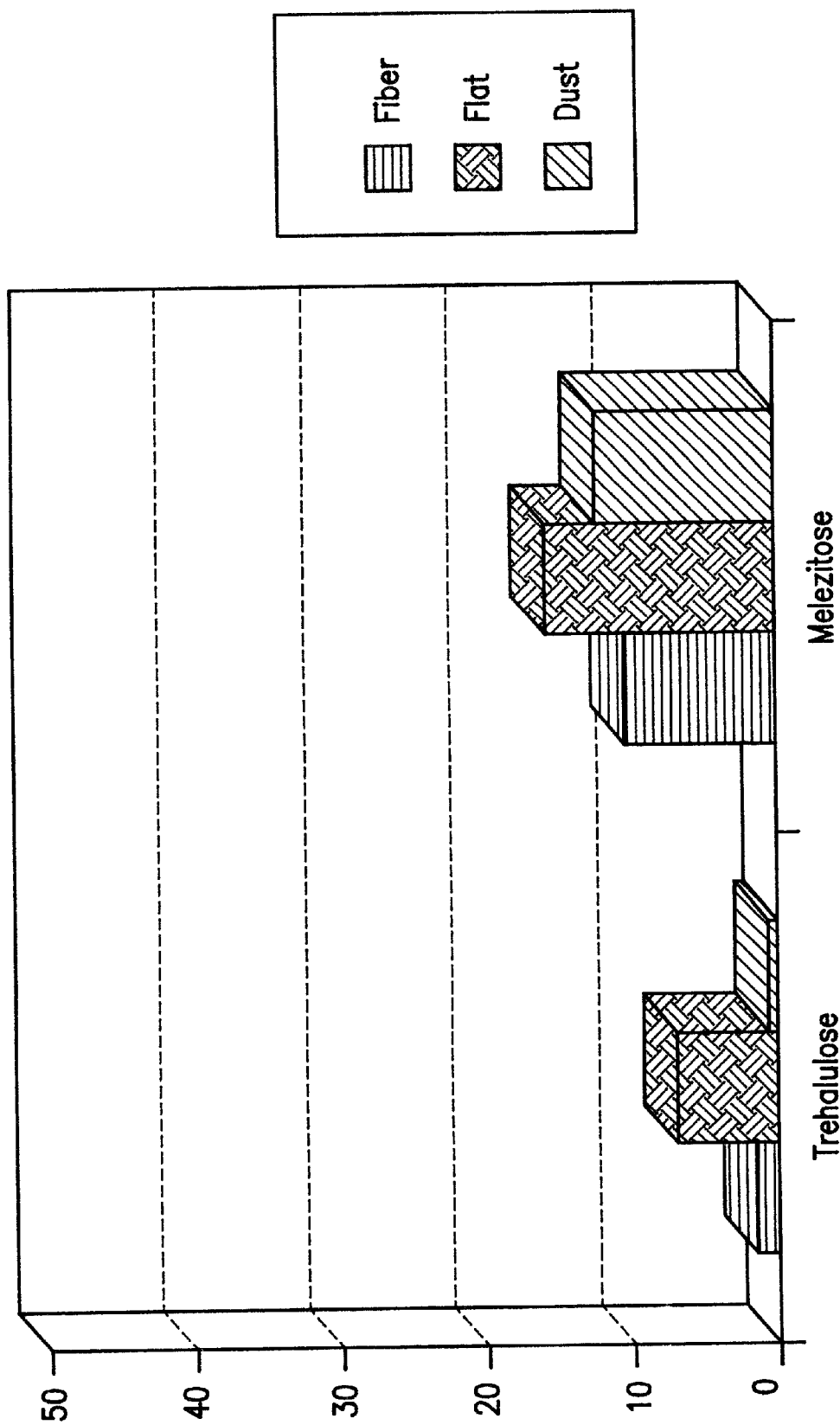
FIG. 4 shows an HPLC profile of non-sticky cotton at an H2SD reading of 2.0.
Figure 5:
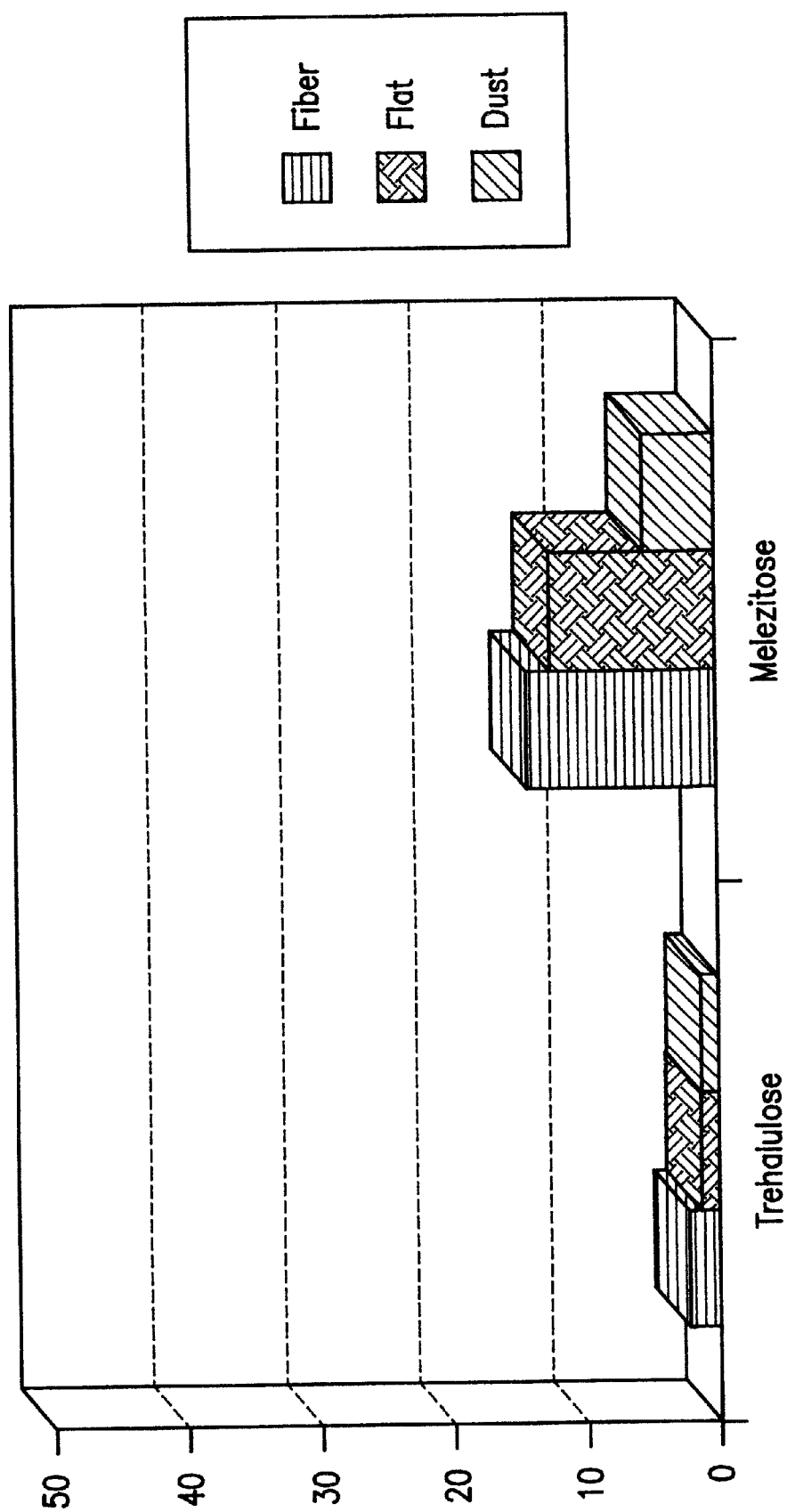
FIG. 5 shows an HPLC profile of non-sticky cotton at an H2SD reading of 2.6.
Figure 6:
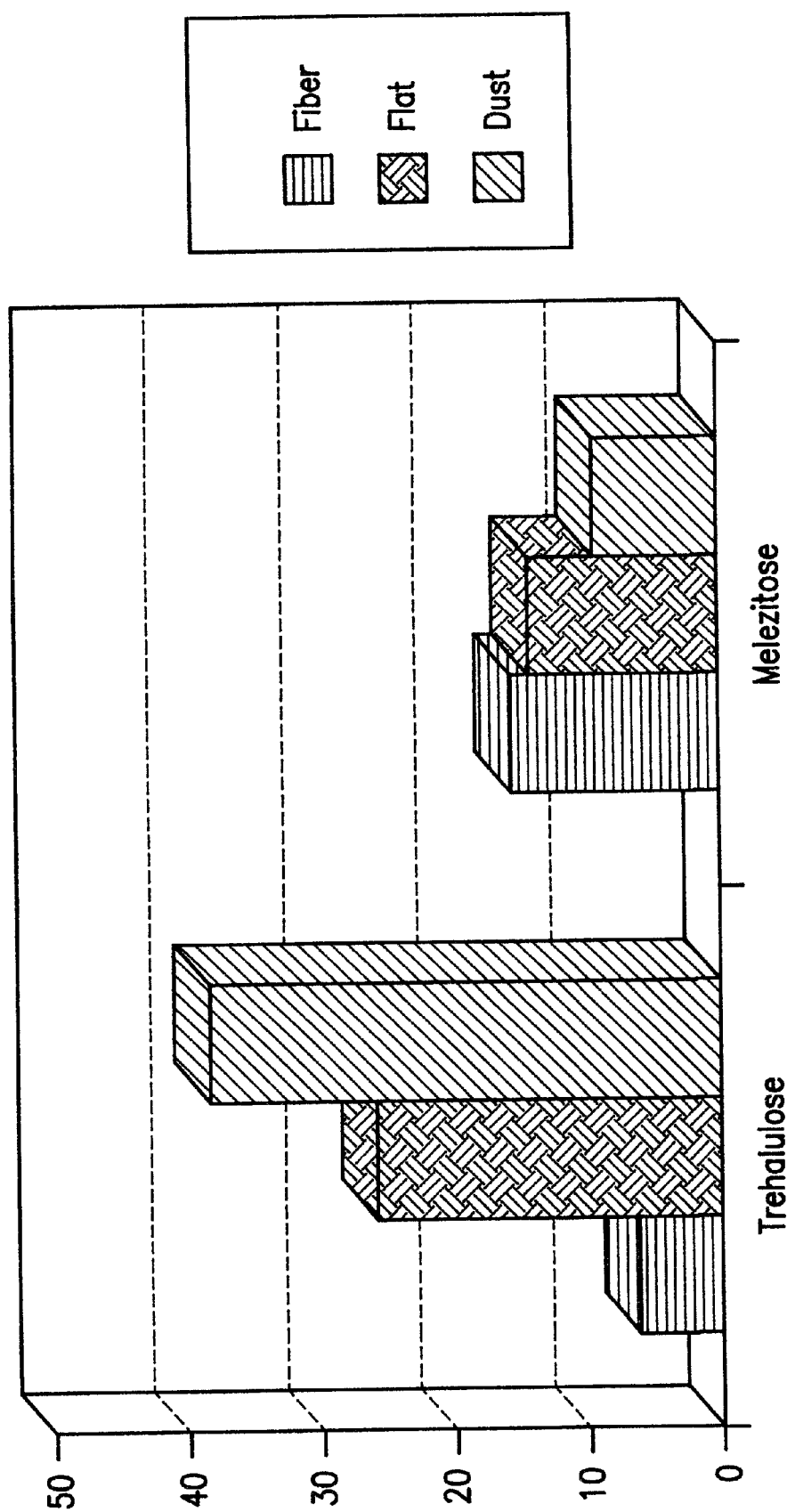
FIG. 6 shows an HPLC profile of sticky cotton at an H2SD reading of 4.0.
Figure 7:
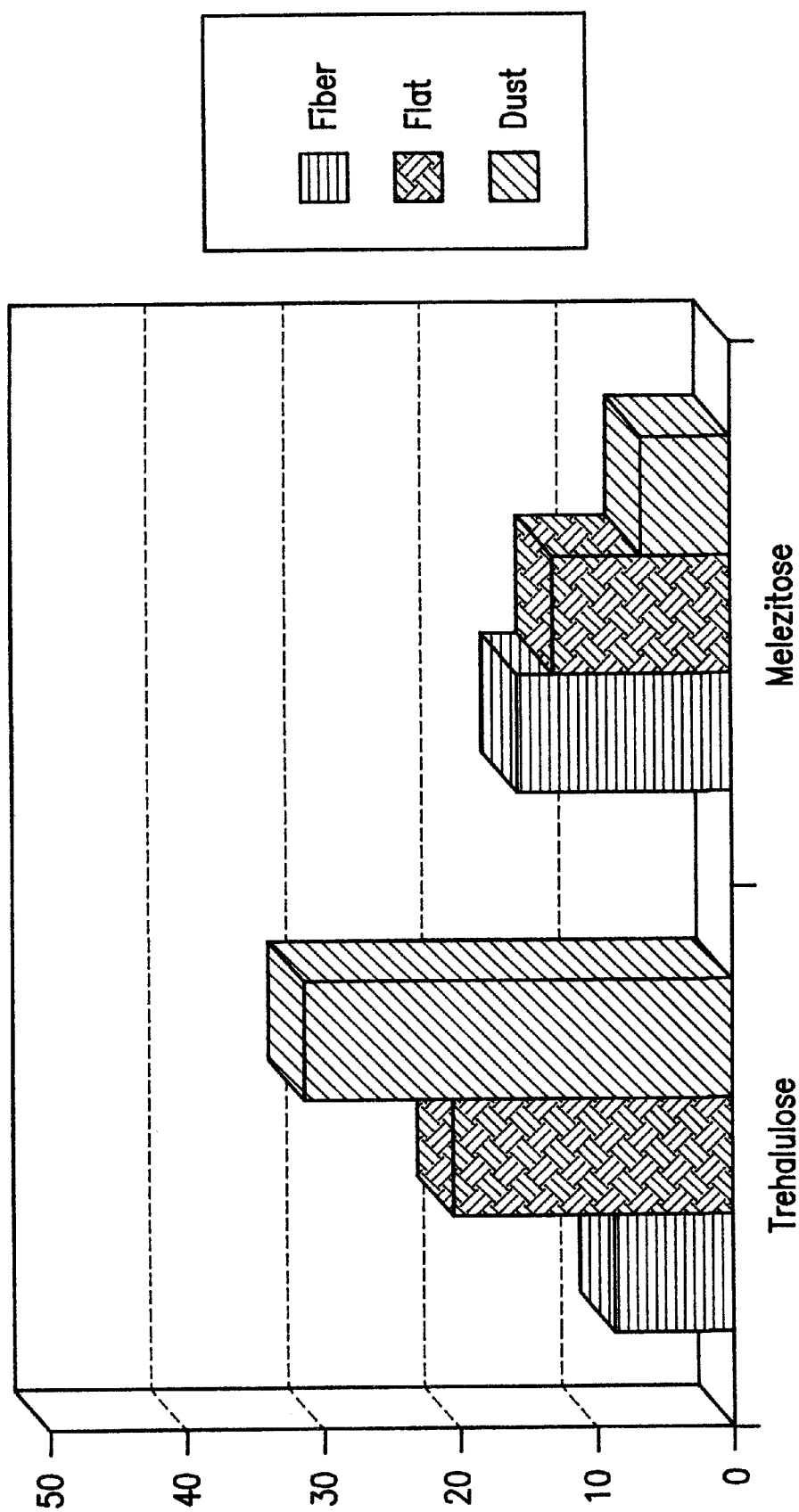
FIG. 7 shows an HPLC profile of sticky cotton at an H2SD reading of 5.6.

In order to elucidate the type of sugars which accumulate on the textile equipment, High Performance Liquid Chromatography (HPLC) tests were performed on fiber, flat wastes and rotor dusts. FIG. 4 and FIG. 5 show the HPLC profiles of non-sticky cotton at High Speed Stickiness Detector (H2SD) readings of 2.0 and 2.6, respectively. FIG. 6 and FIG. 7 show the profiles of sticky mixes (low levels of stickiness—spinable mixes) at H2SD readings of 4.0 and 5.6, respectively. It was found that trehalulose, white fly dominant sugar, becomes more concentrated in both flat wastes and rotor dusts.

In another experiment, contaminated cotton was blended with polyester. The mixture did not reduce the stickiness impact as expected but rather made the problem worst.

Figure 8:
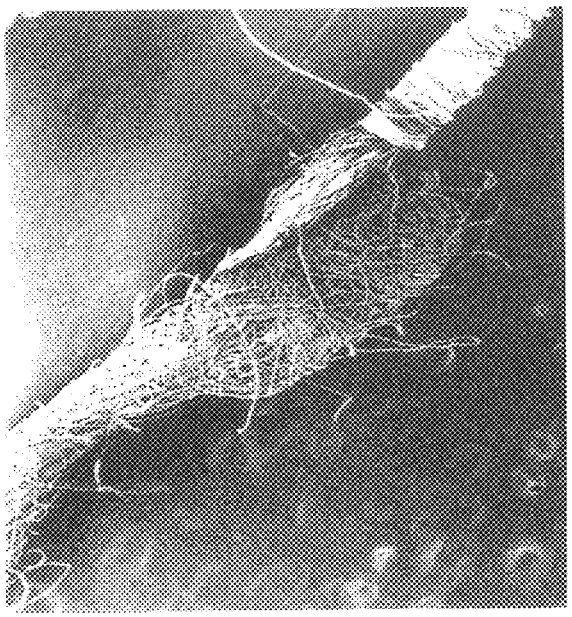
FIG. 8 shows yarn breakage that occurs during the processing of cotton/polyester blends.
Figure 8:
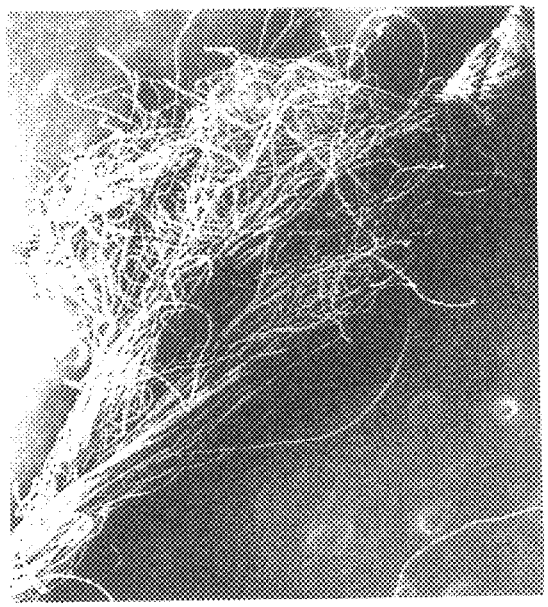
Figure 9:
FIG. 9 shows an amorphous substance on the cotton/polyester blend that causes the defect in the yarn structure.
Figure 10A:
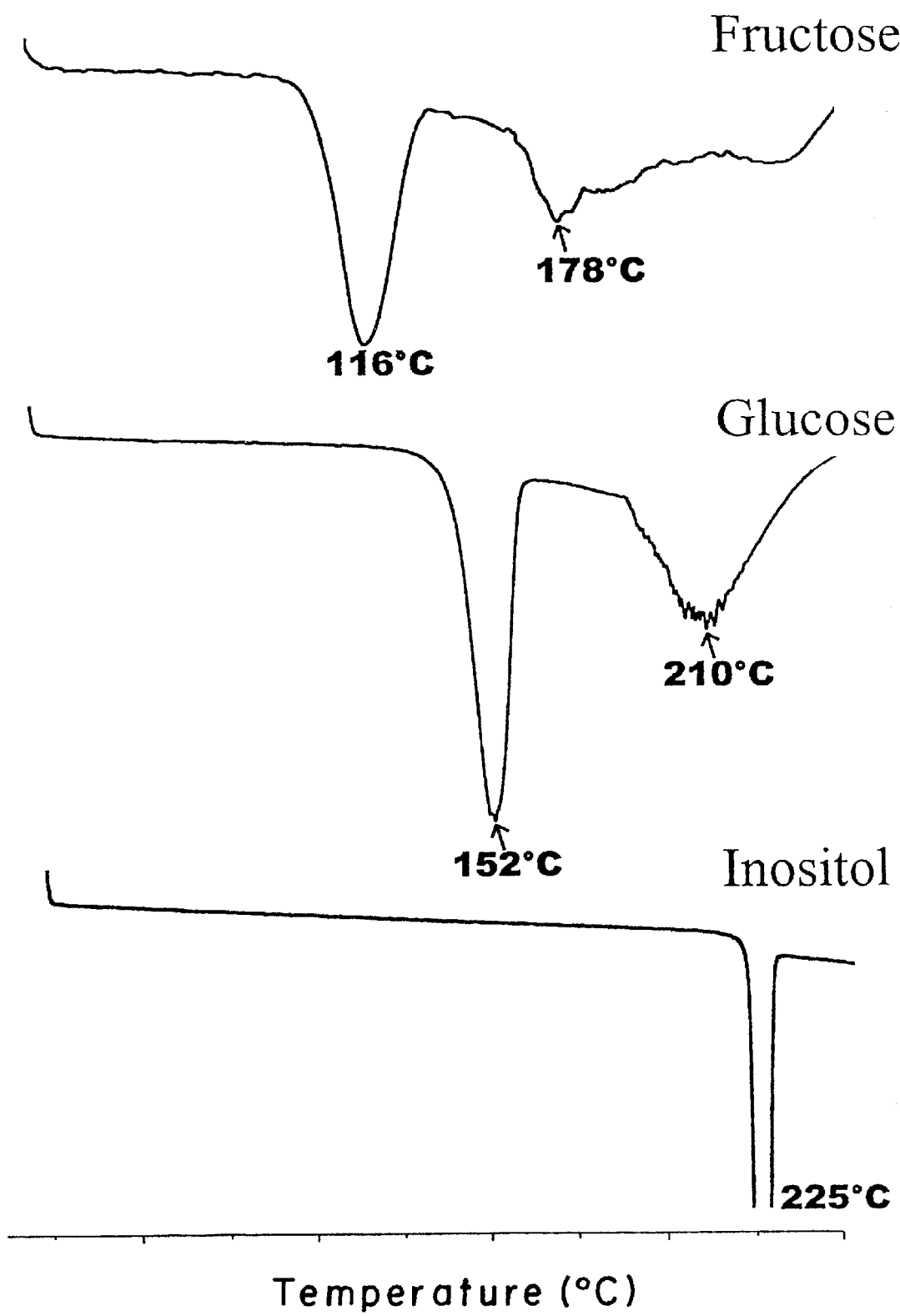
FIGS. 10a–c show Differential Scanning Calorimetry profiles for various sugars: a) fructose, glucose and inositol; b) trehalose, trehalulose and turanose; and c) melezitose and sucrose.
Figure 10B:
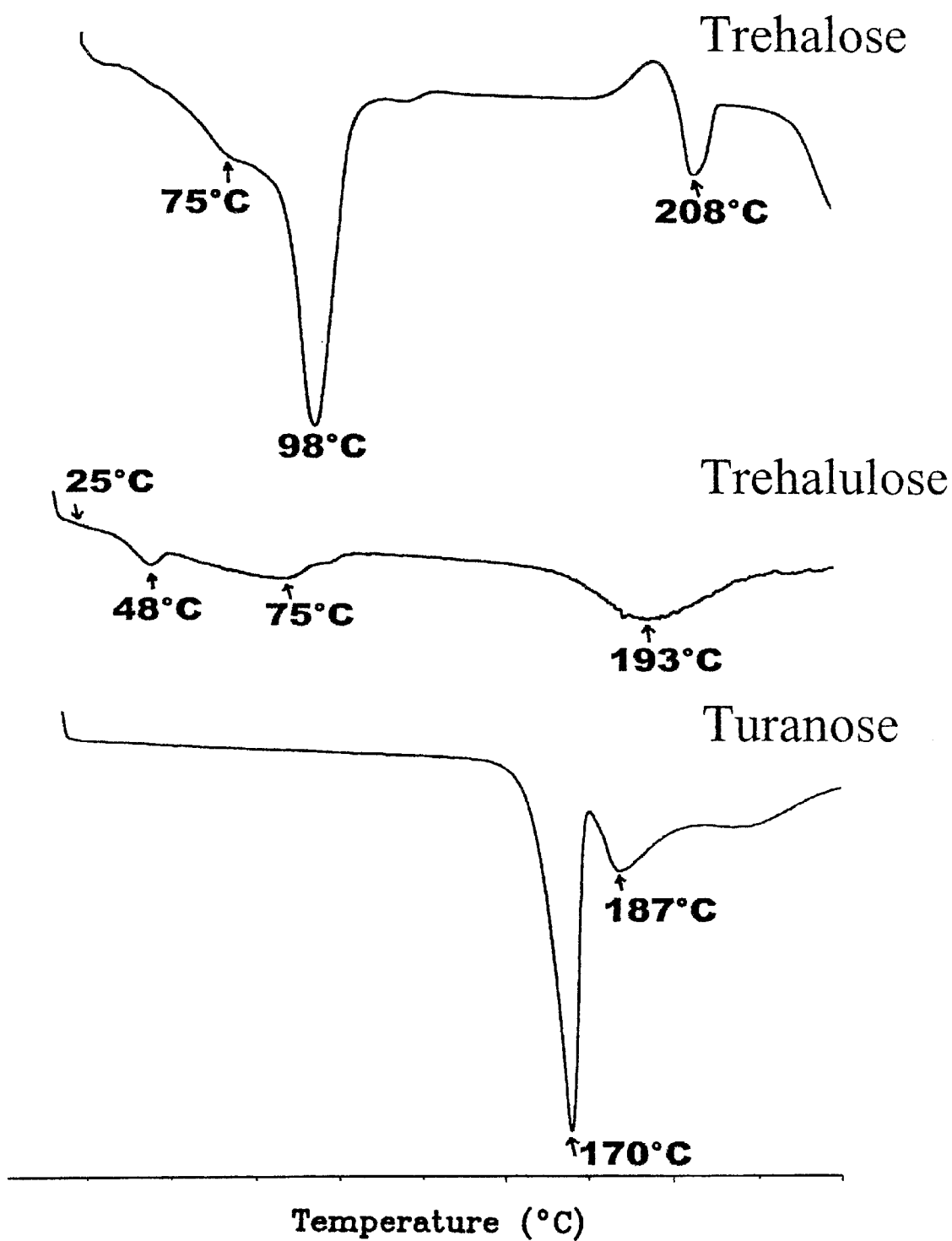
Figure 10C:
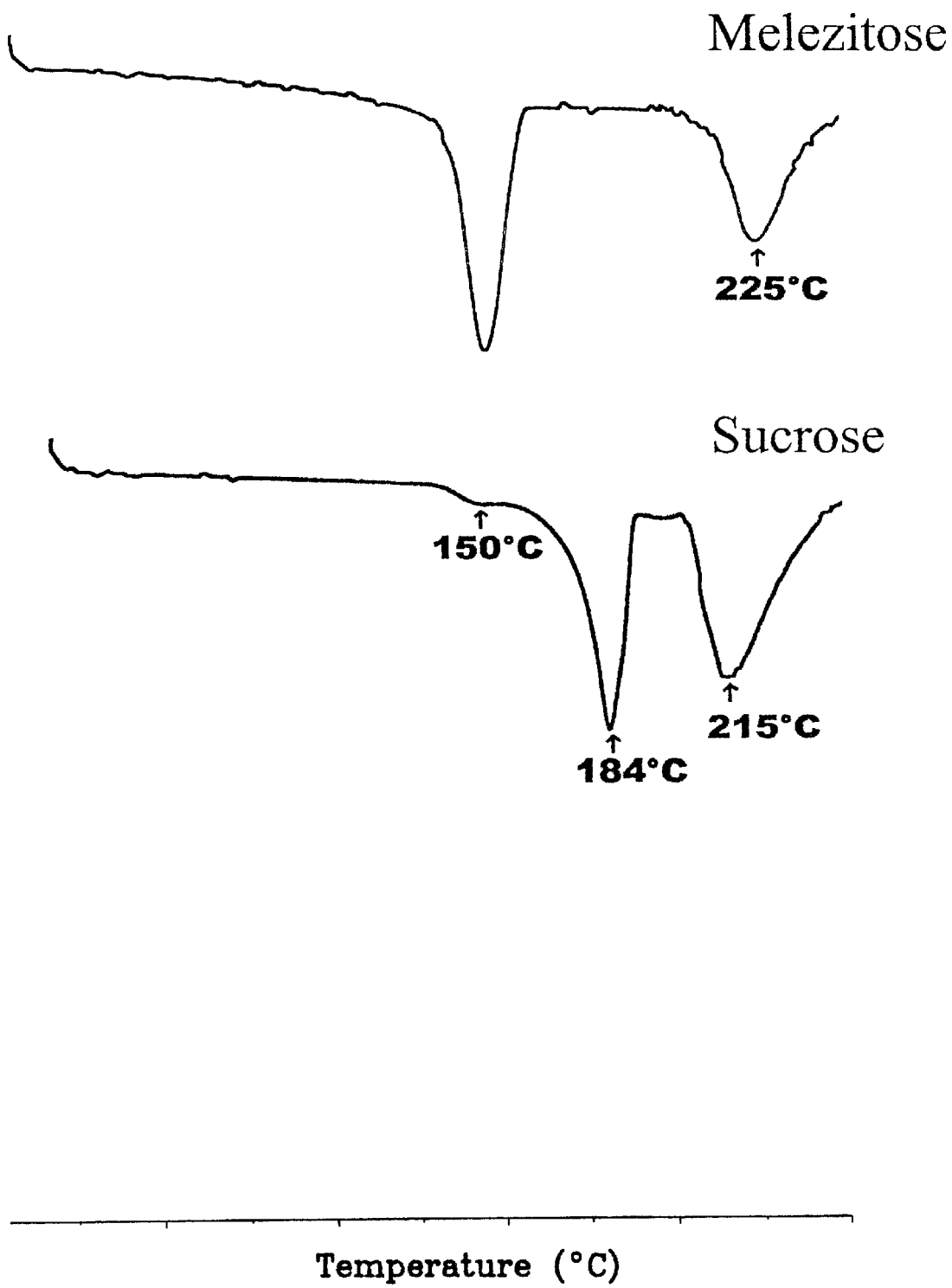

Indeed, a large number of ends-down (yarn breakage) formation during the processing of cotton/polyester blend (35/65) (FIG. 8) occurred. Scanning Electron Microscopy (SEM) was used to examine the cause of the ends-downs. As shown on FIG. 9, the fibers stick together by means of an amorphous substance on which other substances stick, causing defects in the yarn structure and leading to yarn breakage. The ends-down could be related to the structural changes of some sugars during the fiber processing. This is based on the fact that the frictional forces involved in the textile processing lead to a significant increase of the temperature, as shown in FIG. 9b, affecting, therefore, the sugar properties. Consequently, Differential Scanning Calorimetry (DSC) profiles were recorded on the following sugars (non-hydrated state): fructose, glucose, inositol, trehalose, trehalulose, turanose, melezitose and sucrose. FIG. 10a shows the DSC profiles for fructose, glucose and inositol. FIG. 10b shows the DSC profiles for trehalose, trehalulose and turanose. FIG. 10c shows the DSC profile for melezitose and sucrose. All of these sugars are known to be present on contaminated cottons. Among the sugars tested, trehalulose is the only one having a low melting point (around 48° C.).

Figure 11A:
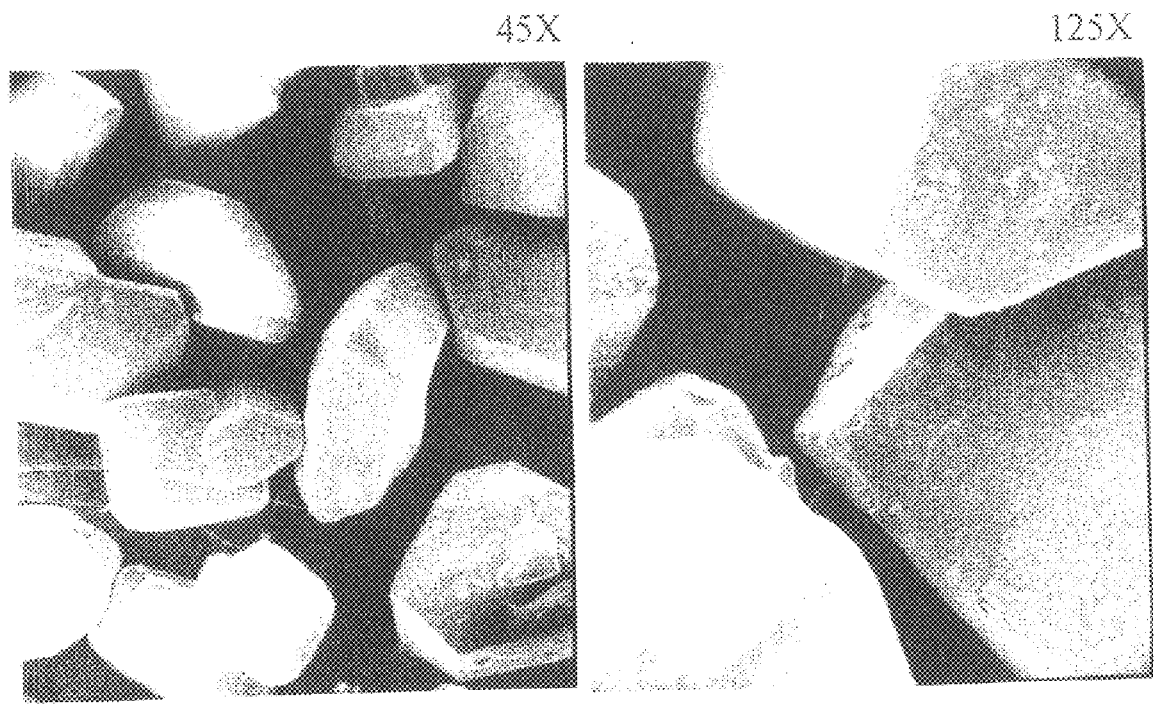
FIGS. 11a–c show SEM pictures of hydrated sugars: a) sucrose; b) melezitose; and c) trehalulose.
Figure 11B:
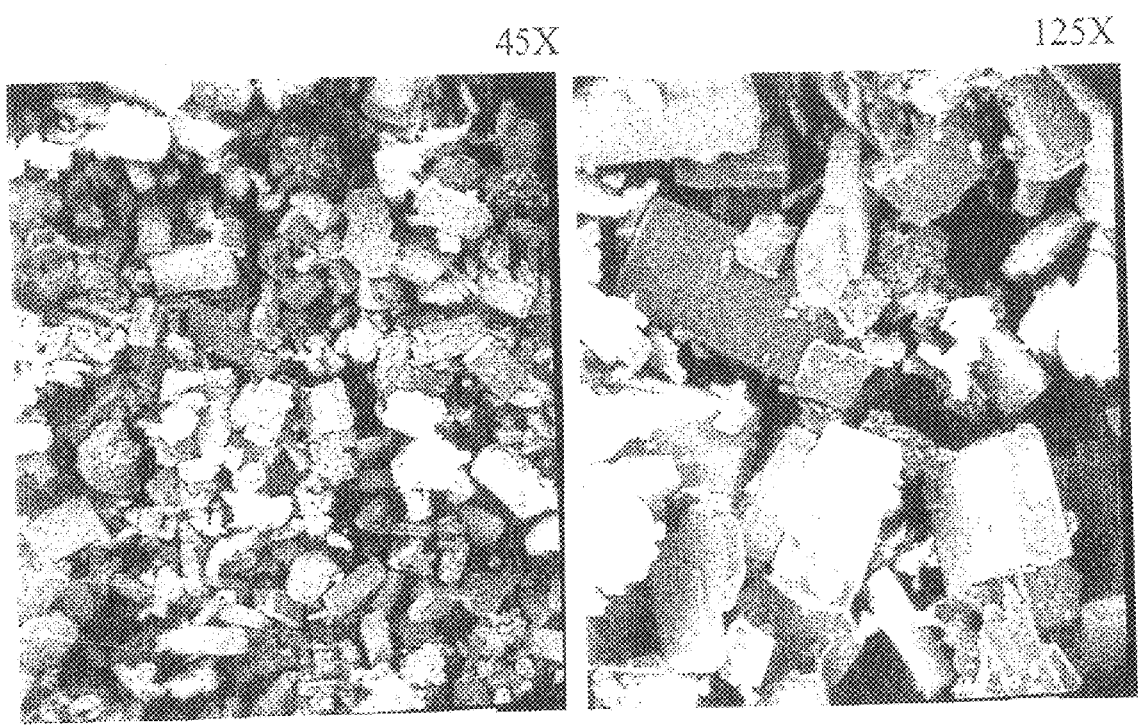
Figure 11C:
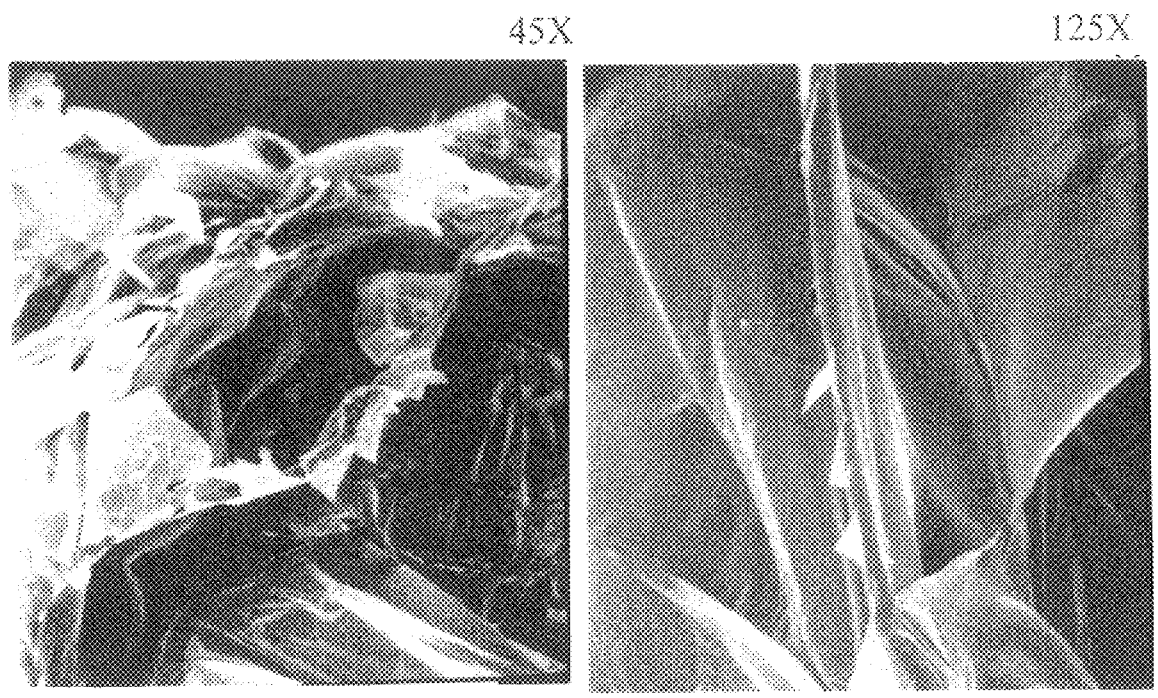
Figure 12A:
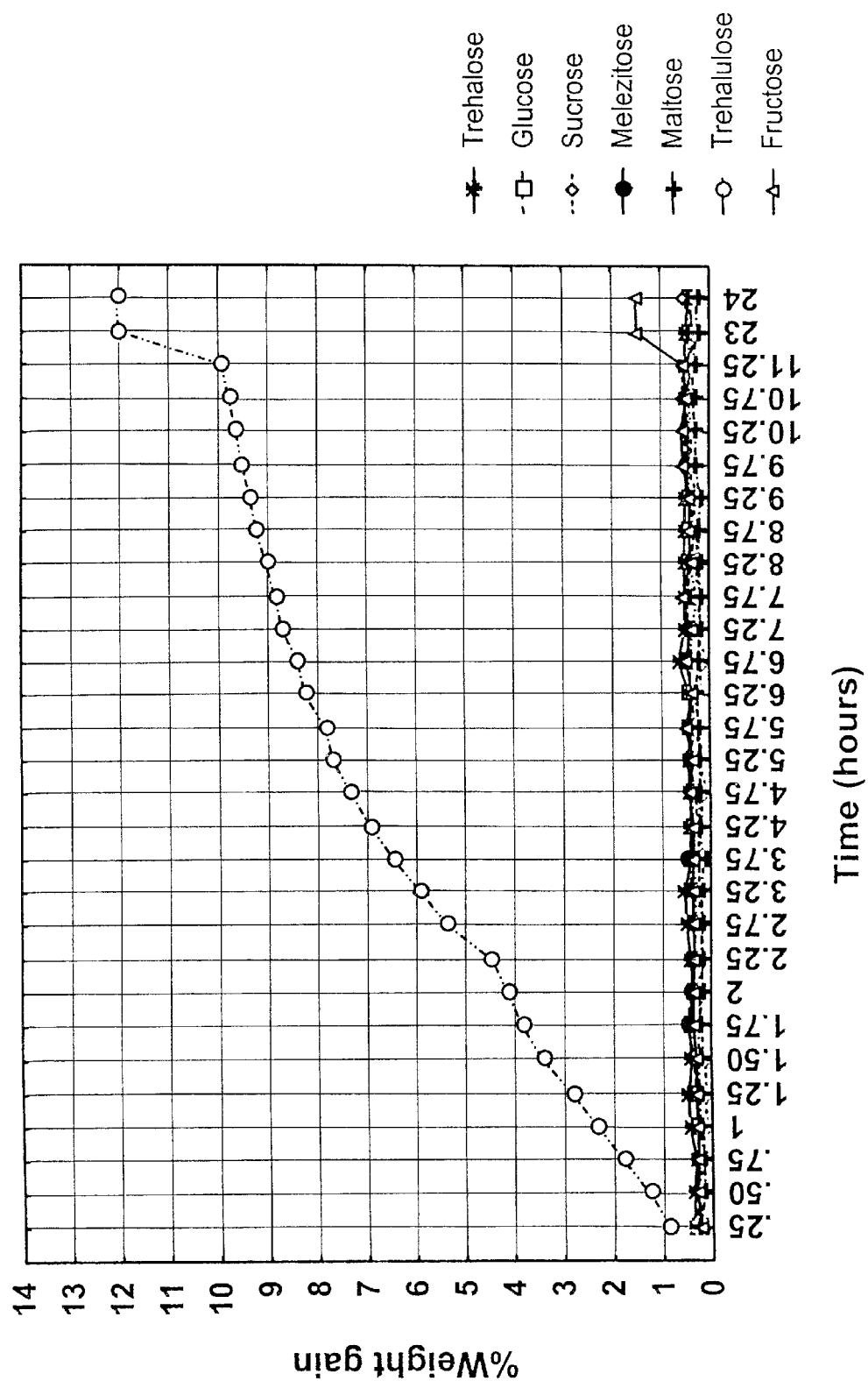
FIGS. 12a–b show the hydration kinetics of known sugars: a) trehalose, glucose, sucrose, melezitose, maltose, trehalulose and fructose; b) trehalulose and fructose at 65% humidity and 70° C.
Figure 12B:
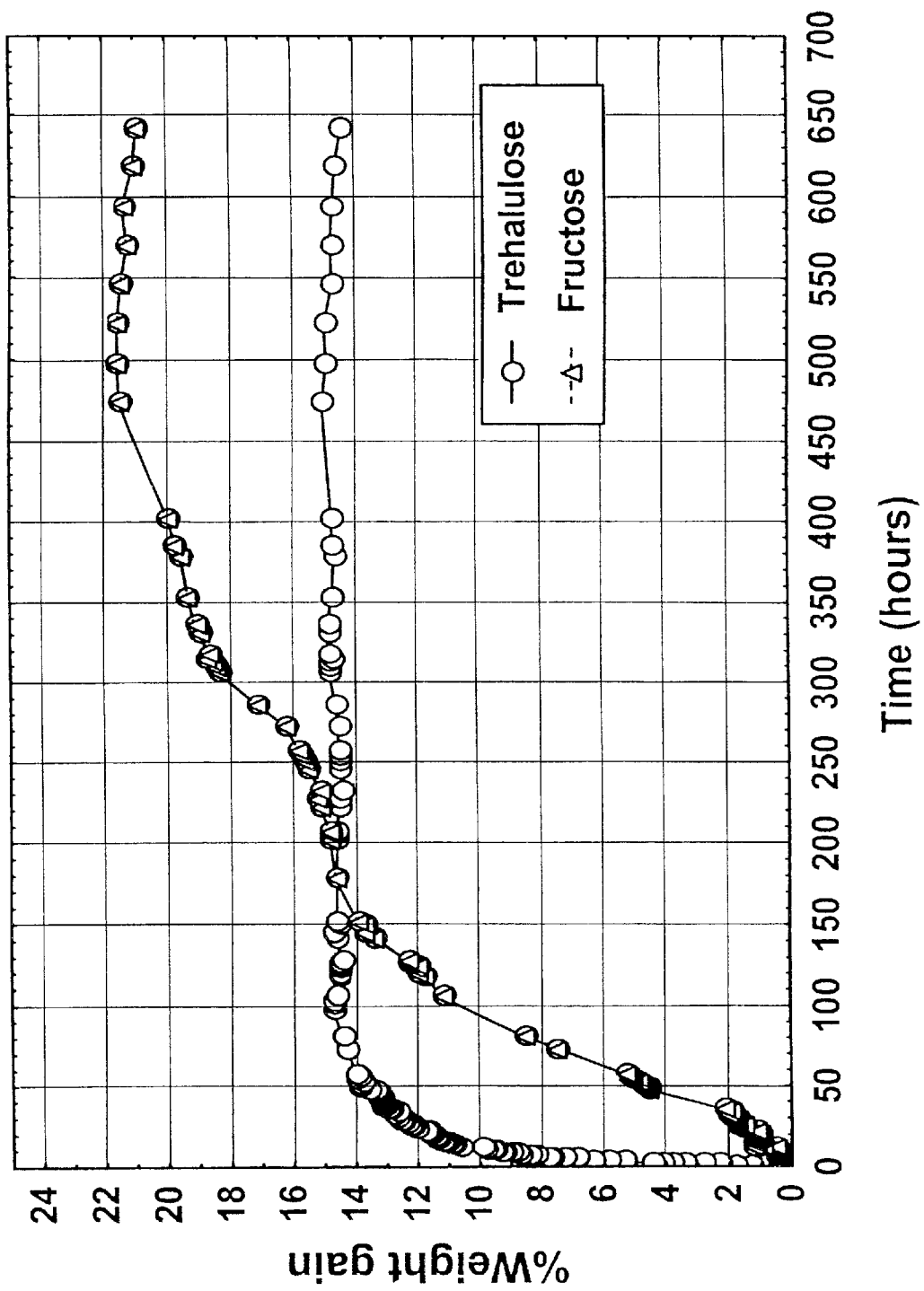

FIGS. 11a–c show SEM pictures of hydrated sugars. FIG. 11a shows SEM pictures of hydrated sucrose, the sugar involved in stickiness from physiological origin. FIG. 11b shows SEM pictures of hydrated melezitose, the sugar involved in stickiness coming from aphids and white fly. FIG. 11c shows SEM pictures of hydrated trehalulose, the sugar involved in stickiness coming from white flies. Sucrose and melezitose remain crystalline even in their hydrated state. However, trehalulose appears to have an amorphous structure (film-like) even in its dry state. In addition, trehalulose and fructose are highly hygroscopic sugars. FIG. 12a shows the hydration kinetics of known sugars such as trehalose, glucose, sucrose, melezitose, maltose, trehalulose and fructose. After conditioning dry sugar samples at 65% relative humidity and 70° C., the quantity of adsorbed water at equilibrium was about 15% for trehalulose and 22% for fructose, corresponding to 3 and 2 molecules of water, respectively, as shown in FIG. 12b. At room temperature and atmospheric pressure, the hydration is not reversible for trehalulose but is for fructose.

In order to achieve a realistic understanding of the cotton stickiness problems that occur in the cotton mill due to trehalulose, a testing method showing the level of stickiness at various temperatures was developed. The testing of the cotton at various temperatures may be accomplished by using any appropriate testing device capable of conducting testing at two or more temperatures. Existing instruments, such as the FCT and H2SD, may be modified or adapted to test cotton stickiness at more than one temperature. Since the normalized manufacturer setting for the hot plate of the H2SD is 54° C., radical design variations would be necessary to perform the multi-temperature testing at multiple temperatures such as 27° C., 34° C., 40° C., 54° C. and 67° C. The general design for the multi-temperature testing apparatus includes a flat or cylindrical heating element, which is in contact with the sample surface. In addition, this element has to be able to deliver temperatures in the range of 10° C. to 120° C. The heating element contains two or more sub-elements having a temperature differential of at least 10° C. The two or more sub-units of the heating element simultaneously exert a pressure on the sample surface. The combined effect of heat and pressure selectively renders the sugar contaminants sticky, depending on their origin. The lowest temperature will render the white flies honeydew stickier than the other types of contaminants. The highest temperature will render all the sugar-contaminated cottons sticky. The differential in two or more readings will indicate the type of processing troubles to be expected in the mill.

The samples for testing are prepared by means of any mechanical device able to produce a smooth surface sample, such as a rotor-type opener, an Aero Mechanical Individualiser, or a needle-type fiber blender. The mechanical device could be independent or integrated in the measurement system.

The testing conditions of the sample are preferably 21° C.±1° C. and 65%±2% relative humidity (RH) or 55%±2% RH. The test results and the relation test results-spinning performances are RH-dependant.

The sticky deposits are preferably deposited directly onto the surface of the heating elements. Alternatively, the sticky deposits are deposited on any type of disposable material such as aluminum, paper or plastic foil.

If high temperatures are used, a cooling element will be necessary in order to lower the honeydew temperature before removing the non-sticky material. The cooling of the sample is preferably attained by either a cold pressure element (flat or cylindrical) at laboratory temperature or by airflow.

The removal of the non-sticky materials from the heating element or the disposable foils are preferably obtained by means of brushes, airflow, vacuum or a combination of the pre-mentioned techniques.

The detection of the sticky deposits may be obtained by any known suitable method, preferably by visual inspection, scanner technologies or cameras. Additionally, special wavelength in the visible, UV or infrared spectra may be advantageously utilized to render the sticky deposits more easily detectable. Various techniques are also used to count and size the sticky deposits, preferably visual counting or image processing.

EXAMPLE

Figure 13:
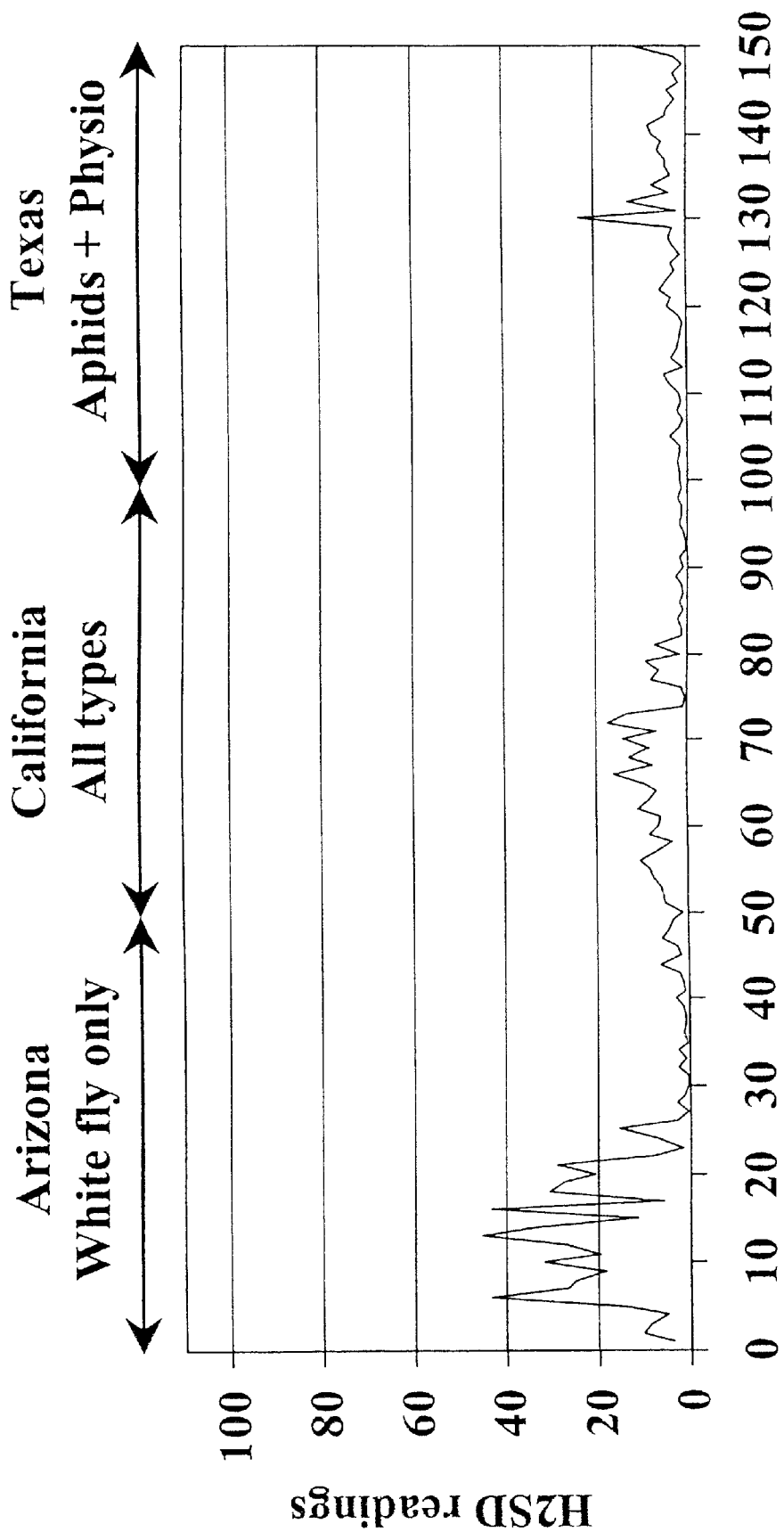
FIG. 13 shows cotton stickiness readings of Arizona, California and Texas cotton bales at 27° C.
Figure 14:
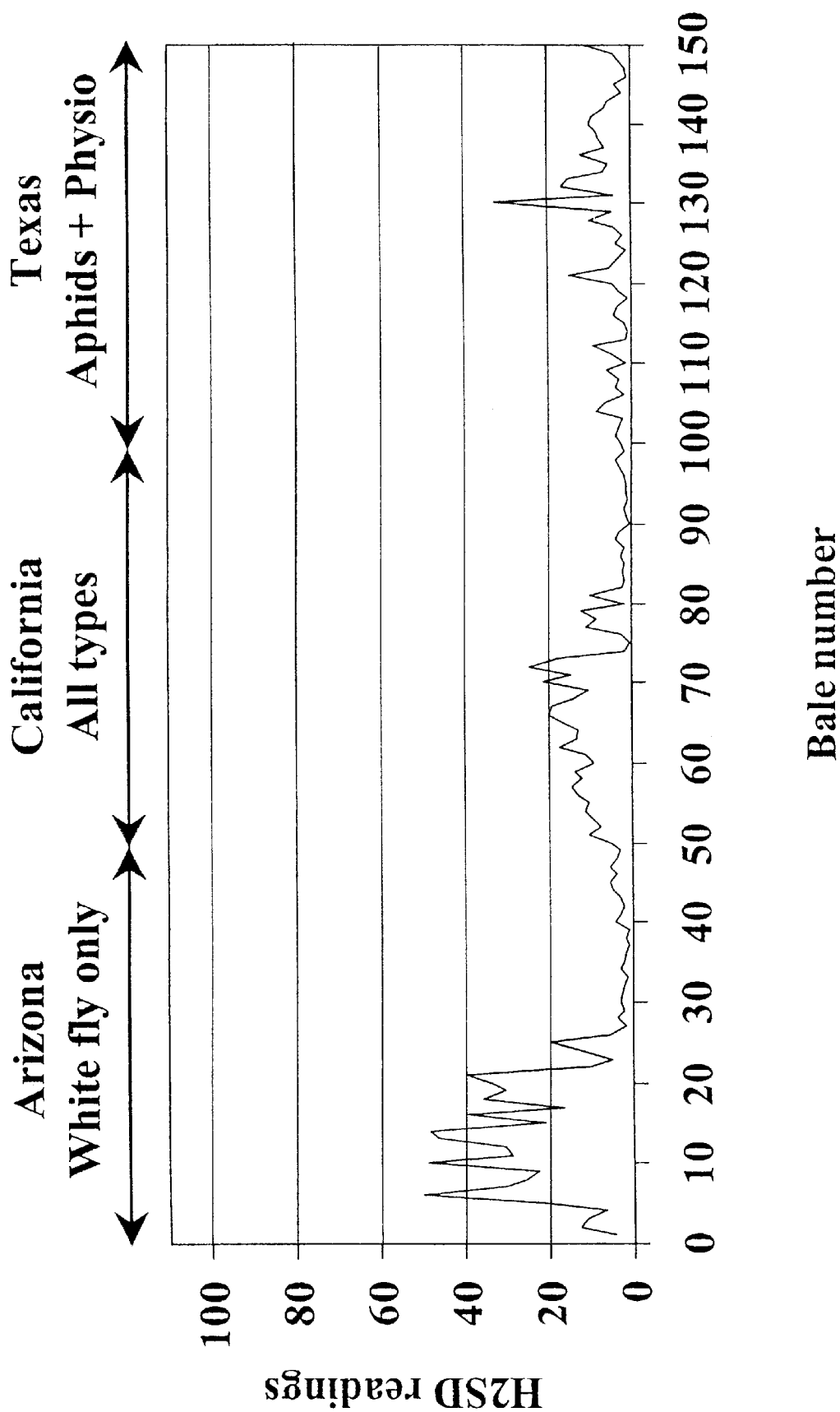
FIG. 14 shows cotton stickiness readings of Arizona, California and Texas cotton bales at 34° C.
Figure 15:
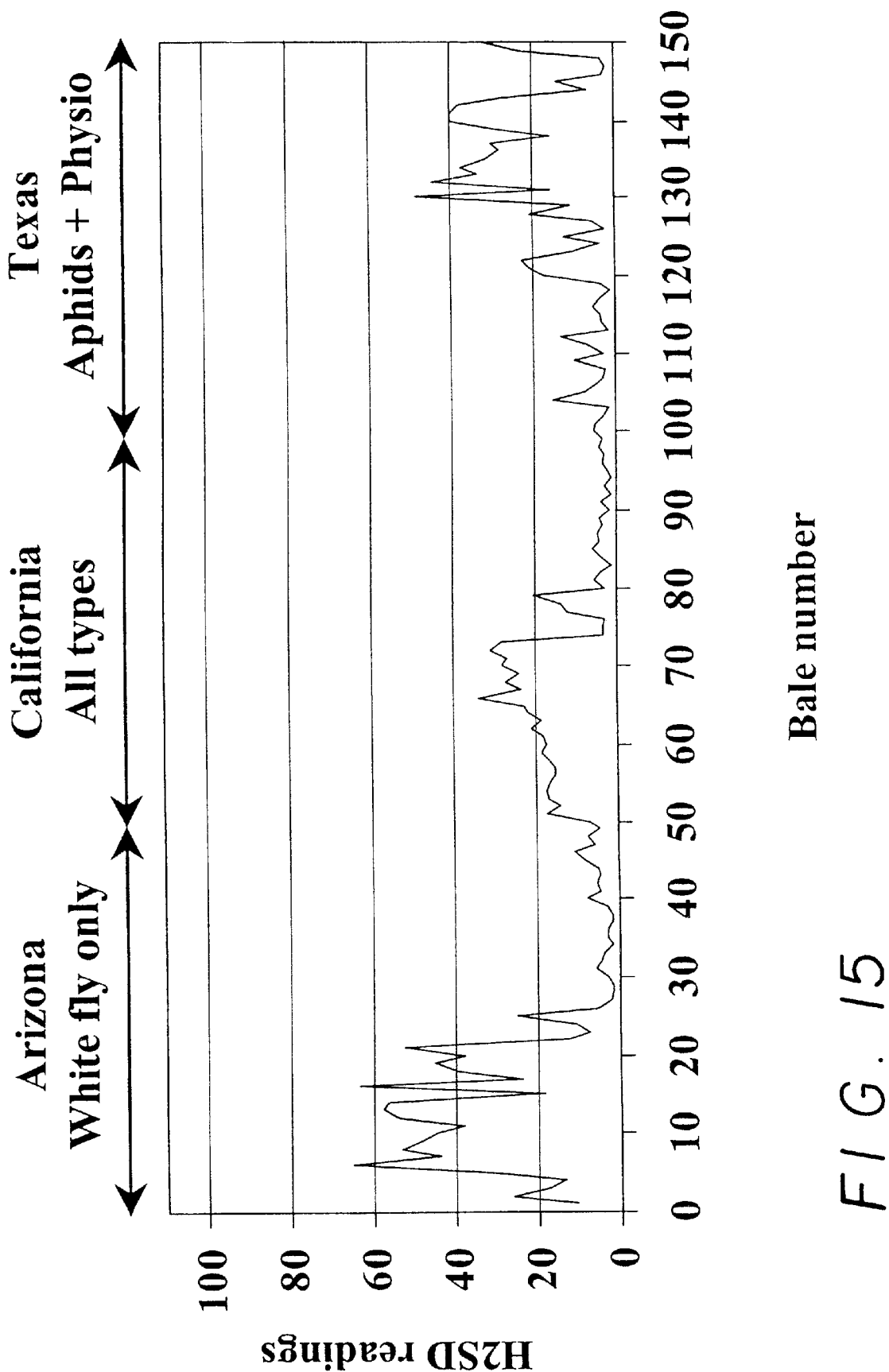
FIG. 15 shows cotton stickiness readings of Arizona, California and Texas cotton bales at 40° C.
Figure 16:
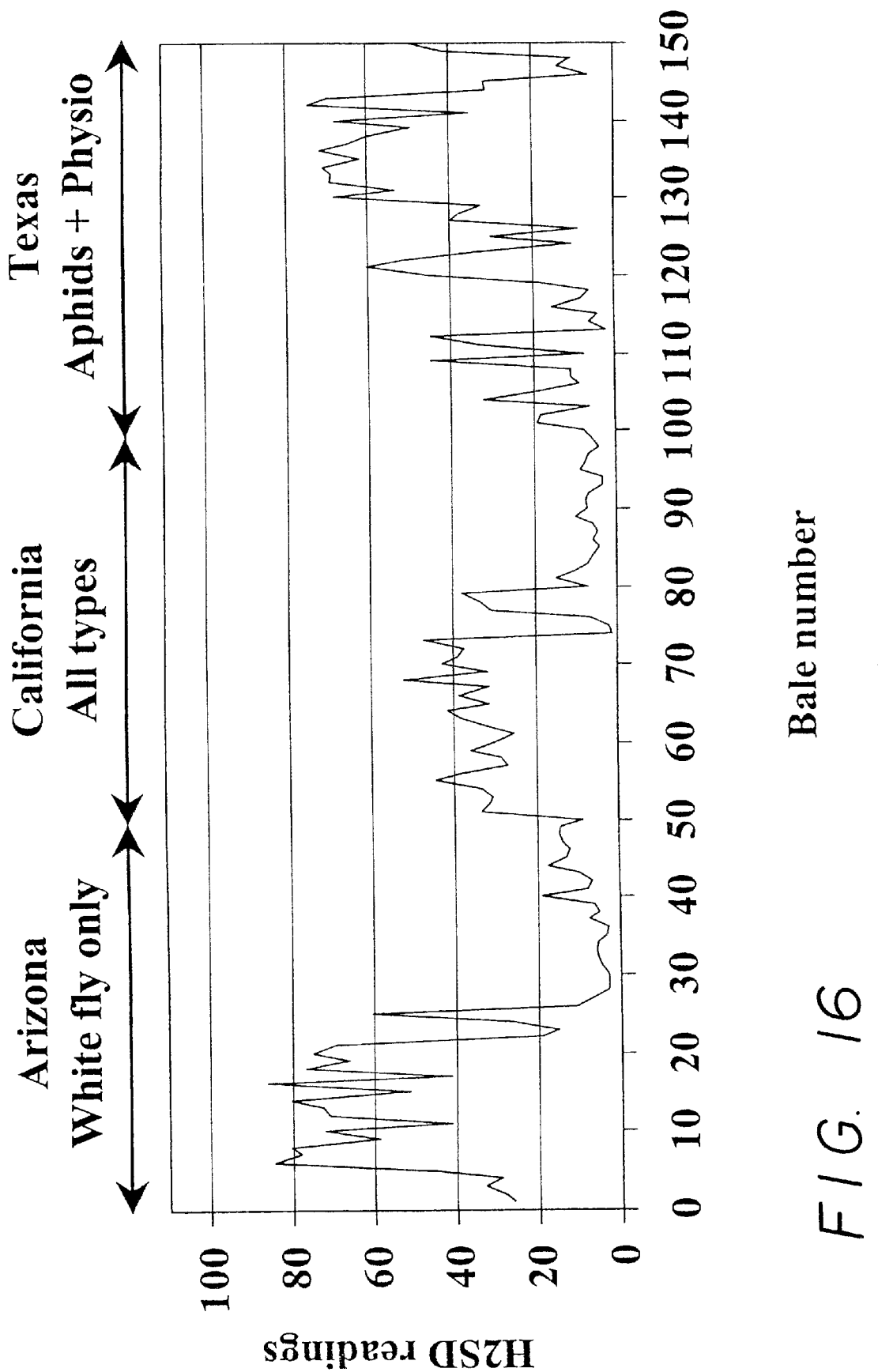
FIG. 16 shows cotton stickiness readings of Arizona, California and Texas cotton bales at 54° C.
Figure 17:
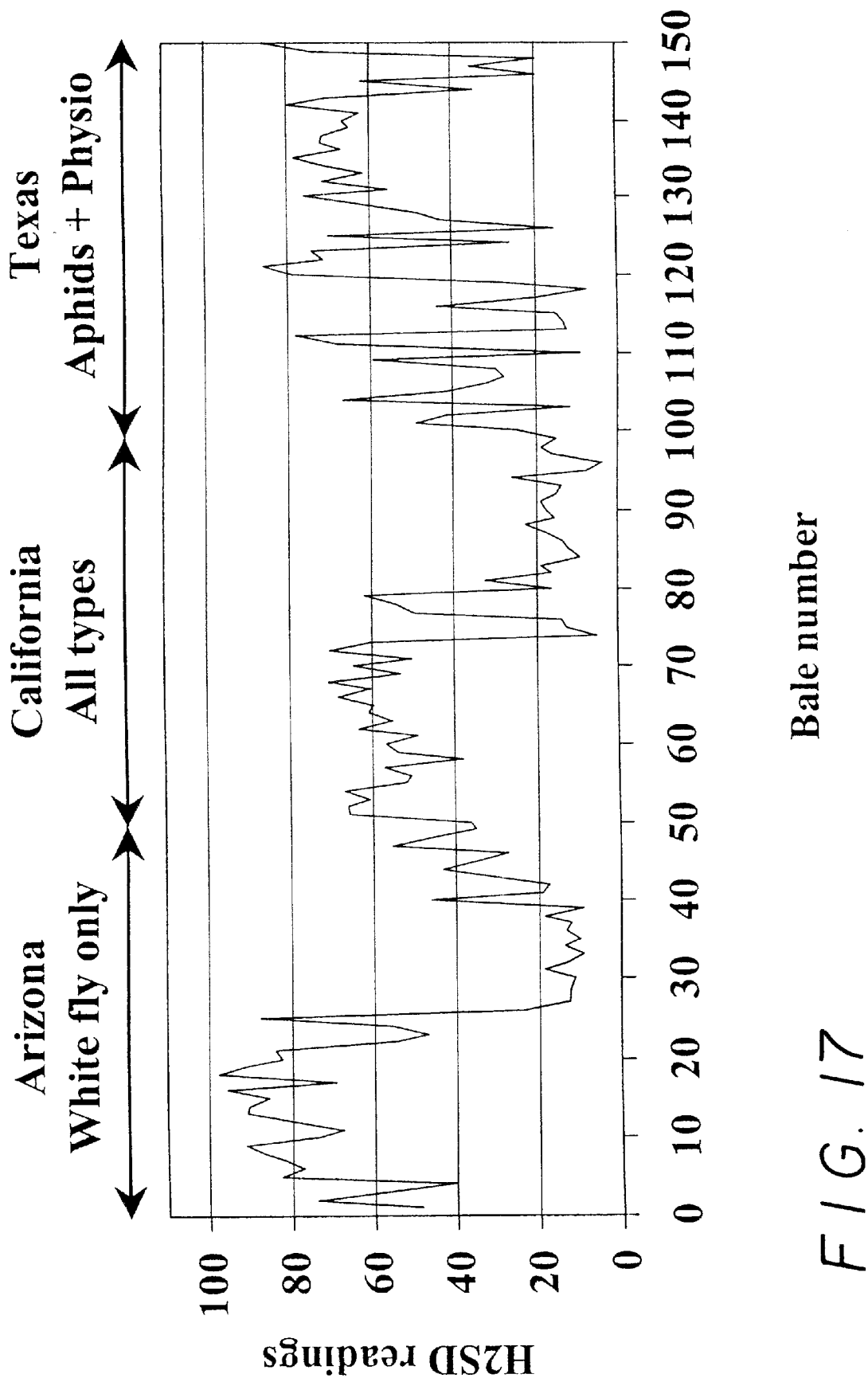
FIG. 17 shows cotton stickiness readings of Arizona, California and Texas cotton bales at 67° C.
Figure 18:
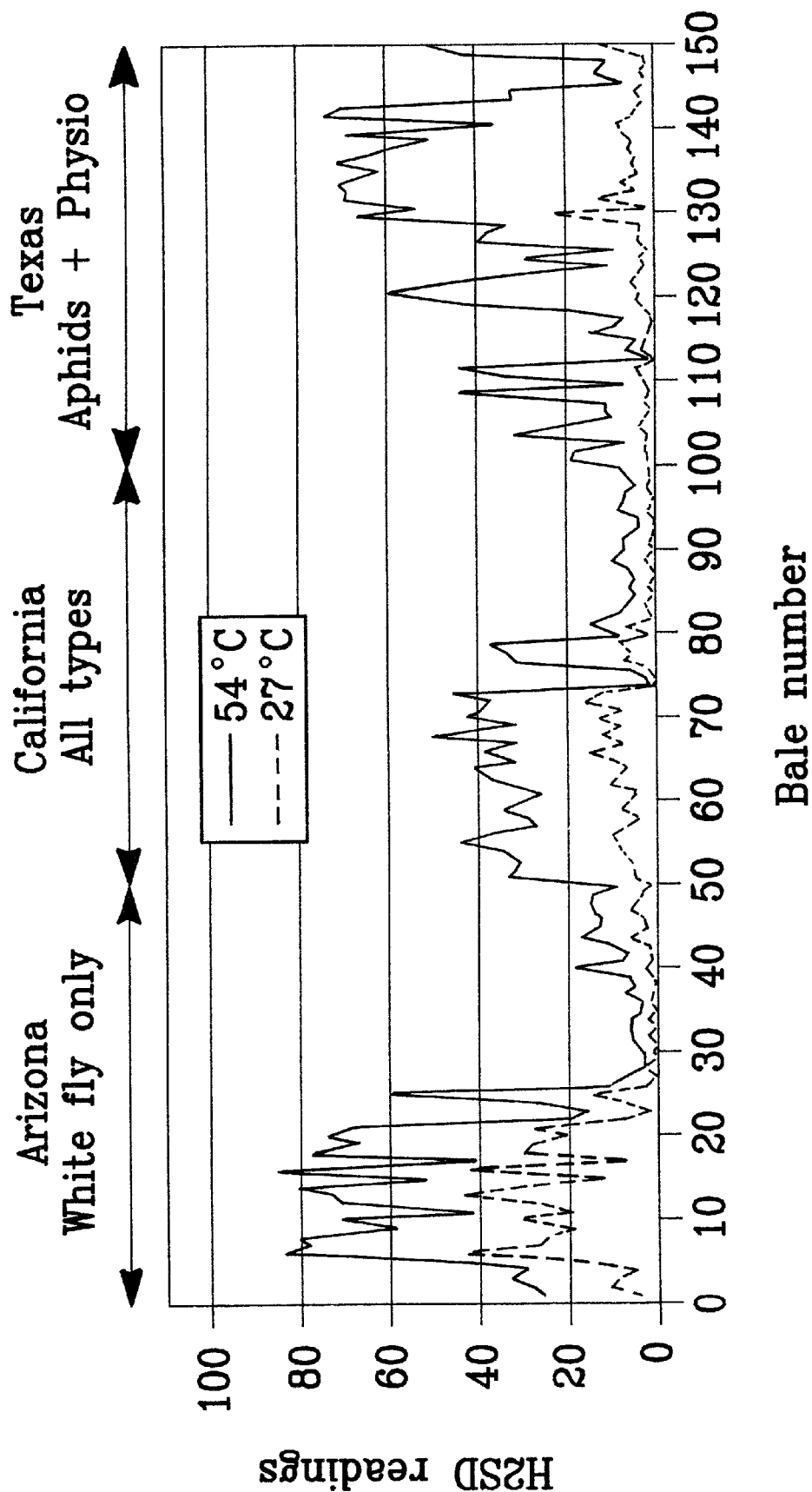
FIG. 18 shows cotton stickiness readings of Arizona, California and Texas cotton bales at 27° C. and 54° C.

One hundred and fifty cotton bales representing a wide range of stickiness and different types of contamination, i.e. white fly, aphid and physiological sugars, were selected for multi-temperature cotton stickiness testing. The samples are from Arizona (known to have important white fly populations and very little to no aphids), California (where both types of insects coexist), and Texas (where large populations of aphids exist and very little to no white flies). In addition, for Texas mainly, high physiological sugar contents could be obtained after a freeze. This could also happen in California but this is a rare event. The bales were sampled (2 samples per bale), and then the samples were tested using the multi-temperature cotton stickiness test. FIG. 13 shows cotton stickiness readings of the three sample bales at 27° C. FIG. 14 shows cotton stickiness readings of the three sample bales at 34° C. FIG. 15 shows cotton stickiness readings of the three sample bales at 40° C. FIG. 16 shows cotton stickiness readings of the three sample bales at 54° C., the standardized temperature reading. FIG. 17 shows cotton stickiness readings of the three sample bales at 67° C. FIG. 18 shows a comparative picture of the cotton stickiness readings of the three sample bales at 27° C. and 54° C. FIGS. 13 to 18 show clearly that:

For Arizona: all the cottons sticky at 54° C. are also sticky at the lowest temperature.

For California, most of the cottons sticky at 54° C. are slightly sticky at the lowest temperature.

For Texas, nearly all the cottons sticky at 54° C. are not sticky at 27° C.

These results demonstrate that by testing at high temperature, nearly all the contaminated cottons become sticky, even the one having little to no trehalulose. Keeping in mind that the temperature of the spinning equipment is by far lower than 54° C., a good stickiness device has to:

Detect the trehalulose-rich honeydew droplets at low temperature (the higher the number of sticky deposits at low temperature, the worse the problems will be at the mill).

Detect the non trehalulose-rich honeydew droplets and physiological sugars at higher temperature (the higher the number of sticky deposits at high temperature, the worse the problems will be at the mill)

Although the present invention has been disclosed in terms of a preferred embodiment, it will be understood that numerous additional modifications and variations could be made thereto without departing from the scope of the invention as defined by the following claims:

What is claimed is:

1. A method for detecting the stickiness of cotton comprising:
   providing a sample of cotton material;
   testing said sample of cotton material at a lower temperature;
   detecting a first amount of sticky spots produced from said testing of said sample of cotton material at said lower temperature;
   testing said sample of cotton material at a higher temperature;
   detecting a second amount of sticky spots produced from said testing of said sample of cotton material at said higher temperature;
   determining a difference in amount between said first amount of sticky spots and said second amount of sticky spots; and
   determining a type of contamination in said sample of cotton material using said difference in amount.

2. The method of claim 1, wherein said lower temperature is less than 54° C.

3. The method of claim 2, wherein said lower temperature is 27° C.

4. The method of claim 2, wherein said lower temperature is 34° C.

5. The method of claim 1, wherein said higher temperature is at least 54° C.

6. The method of claim 1, wherein said sample of cotton material is at a temperature of 21° C.±1° C.

7. The method of claim 6, wherein said sample of cotton material has a relative humidity of 65%±2%.

8. The method of claim 6, wherein said sample of cotton material has a relative humidity of 55%±2%.

9. The method of claim 1, further comprising the step of smoothing said sample of cotton material in a mechanical device prior to testing.

10. The method of claim 1, further comprising the step of providing a disposable material for recording said first and second amount of stickiness.

11. The method of claim 10, further including selecting said disposable material from the group consisting of aluminum, paper and plastic foil.

12. The method of claim 1, wherein the step of detecting a first amount of sticky spots produced from said testing of said sample of cotton material at said lower temperature includes image processing.

13. The method of claim 1, wherein the step of detecting a second amount of sticky spots produced from said testing of said sample of cotton material at said higher temperature includes image processing.

14. The method of claim 1, further comprising the step of providing a heating element to achieve said lower temperature or said higher temperature.

15. The method of claim 14, wherein the step of providing a heating element includes providing heat at a range of 10° C. to 120° C.

16. The method of claim 14, further comprising the step of exerting pressure on a surface of said sample of cotton material between a first sub-unit of said heating element and a second sub-unit of said heating element.

17. The method of claim 1, wherein said detecting of said first amount of sticky spots detects only an amount of trehalulose-rich honeydew droplets in said sample of cotton.

18. The method of claim 1, wherein said detecting of said second amount of sticky spots detects a combined amount of trehalulose-rich honeydew droplets and non-trehalulose-rich honeydew droplets.

19. The method of claim 1, wherein said type of contamination is white fly honeydew.

20. The method of claim 1, wherein said type of contamination is aphid honeydew.

* * * * *